(12) United States Patent
Cha et al.

(10) Patent No.: US 9,351,678 B2
(45) Date of Patent: May 31, 2016

(54) LANCET HOLDER AND LANCET DEVICE INCLUDING THE SAME

(75) Inventors: Geun Sig Cha, Seoul (KR); Hakhyun Nam, Seoul (KR); Eun-Jong Cha, Cheongju-si (KR); Kyung-Ah Kim, Cheongju-si (KR)

(73) Assignee: I-SEN, INC., Seoul (KR)

( * ) Notice: Subject to any disclaimer, the term of this patent is extended or adjusted under 35 U.S.C. 154(b) by 285 days.

(21) Appl. No.: 13/995,153

(22) PCT Filed: Sep. 20, 2011

(86) PCT No.: PCT/KR2011/006932
§ 371 (c)(1),
(2), (4) Date: Jun. 17, 2013

(87) PCT Pub. No.: WO2012/081806
PCT Pub. Date: Jun. 21, 2012

(65) Prior Publication Data
US 2013/0267977 A1    Oct. 10, 2013

(30) Foreign Application Priority Data

Dec. 15, 2010  (KR) .................. 10-2010-0128355

(51) Int. Cl.
*A61B 17/34* (2006.01)
*A61B 5/151* (2006.01)
*A61B 5/15* (2006.01)

(52) U.S. Cl.
CPC ........... *A61B 5/15101* (2013.01); *A61B 5/1411* (2013.01); *A61B 5/1513* (2013.01); *A61B 5/1519* (2013.01); *A61B 5/15117* (2013.01); *A61B 5/150732* (2013.01); *A61B 5/150022* (2013.01); *A61B 5/15113* (2013.01); *A61B 5/15194* (2013.01); *A61B 5/150412* (2013.01); *A61B 5/150519* (2013.01); *A61B 5/150664* (2013.01)

(58) Field of Classification Search
USPC .................................................. 606/181, 182
See application file for complete search history.

(56) References Cited

U.S. PATENT DOCUMENTS

| 2003/0028126 | A1 | 2/2003 | List | |
|---|---|---|---|---|
| 2006/0247670 | A1* | 11/2006 | LeVaughn et al. | 606/181 |
| 2007/0083222 | A1* | 4/2007 | Schraga | 606/181 |
| 2007/0162063 | A1* | 7/2007 | Marshall et al. | 606/181 |
| 2010/0049233 | A1 | 2/2010 | Shur et al. | |
| 2010/0217300 | A1* | 8/2010 | Kheiri | A61B 5/1411 606/182 |
| 2011/0224712 | A1* | 9/2011 | Winheim et al. | 606/181 |

FOREIGN PATENT DOCUMENTS

| CN | 101048105 A | 10/2007 |
|---|---|---|
| CN | 101346101 A | 1/2009 |
| CN | 101374457 A | 2/2009 |
| EP | 1254632 A1 | 11/2002 |
| EP | 1312308 A1 | 5/2003 |
| EP | 1815792 A1 | 8/2007 |

(Continued)

*Primary Examiner* — Tuan V Nguyen
(74) *Attorney, Agent, or Firm* — McDermott Will & Emery LLP

(57) ABSTRACT

A lancet holder includes a holder body having a lancet seat at one end to mount a lancet and receiving the lancet and elastic fixing portions arranged in pairs to face each other on the inner side of the holder body so that the lancet received in the holder body is vertically held, and elastically fixing the lancet.

6 Claims, 7 Drawing Sheets

(56) References Cited

FOREIGN PATENT DOCUMENTS

| KR | 10-2001-0027981 A | 4/2001 |
| KR | 10-2003-0045846 A | 6/2003 |
| KR | 10-2008-0073782 A | 8/2008 |
| KR | 10-2008-0073790 A | 8/2008 |
| WO | WO-2007/005665 A1 | 1/2007 |
| WO | WO-2010/067501 A1 | 6/2010 |

* cited by examiner

Microlet
Rectangular
cross-section
L=23.05mm

Microlet
Rectangular
cross-section
L=22.40mm

One-touch ultra soft
Rectangular
cross-section
L=23.00mm

Geosang medical
Rectangular
cross-section
L=21.75mm

Abott
Circular cross-section
L=22.80mm

Autolet Impression
Triangular
cross-section
L=22.70mm

LANCET HOLDER AND LANCET DEVICE INCLUDING THE SAME

FIELD OF THE INVENTION

The present invention relates to a lancet holder and a lance device including the same. More particularly, the present invention relates to a lancet holder that is available for all of lancets with different shapes and diameters of the cross-sections and can keep vertical, and a lancet device including the lancet holder.

DESCRIPTION OF THE RELATED ART

In general, chronic diabetics have to measure the blood glucose level by performing a blood glucose test by themselves everyday at home and to perform disease control in order to keep a predetermined blood glucose level.

They have to collect blood for the blood glucose test, and this case, generally, they stick a disposable lancet into the skin of a portion, usually a finger, of their bodies, take and put a small amount of capillary blood onto a strip, and then measure the blood glucose level using a blood glucose meter with the strip mounted.

A lancet device is generally used as the device for taking blood.

The lancet device is composed of a lancet holder mounted with a disposable lancet, a cover that covers a lancet and has a hole through which only the tip of a needle protrudes to penetrate a skin, and a spring and a releasing member that provide a penetration force. The disposable lancet has a blood-taking needle at one end of a lancet body and a protection cap is combined with the blood-taking needle.

According to the lancet devices having this configuration in the related art, a user removes the cover from a lancet device, mounts a disposable lancet onto the lancet holder, attaches the cover with the spring compressed, brings the lancet in close contact with a portion with many capillaries such as fingers, and then releases the disposable lancet by pulling a releasing switch, such that the lancet penetrates the skin.

It is preferable for the blood-taking needle to instantaneously protrude vertically through the through-hole of the cover when releasing the lancet, in order to reduce the pain of the subject.

That is, when the lancet is mounted on the lancet holder at an angle to a side, the traveling direction of the blood-taking needle is likely to be not straight, but inclined in releasing, such that there is a problem in that the entrance area on the skin increases, and accordingly, the blood-taking needle damages the skin and cannot take blood from deep inside the skin.

Further, since most lancets on the market have various cross-sections, such as a rectangle, a circle, and a triangle, and are a little different in diameter of 21.75-23.05 mm, as shown in FIG. 1, there is a problem in that it is required to use only the exclusive lancet holders.

DISCLOSURE

Technical Problem

The present invention has been made in an effort to provide a lancet holder having advantages of being available for all of lancets with different cross-sections and diameters and of being able to keep the lancets vertical, and a lancet device including the lancet holder.

Technical Solution

An exemplary embodiment of the present invention provides a lance holder including: a holder body having a lancet seat at one end to mount a lancet and receiving the lancet; and elastic fixing portions arranged in pairs to face each other on the inner side of the holder body so that the lancet received in the holder body is vertically held, and elastically fixing the lancet.

As described above, according to the present invention, the lancet holder can accurately keep all of lancets vertical, even if the lancets are different in cross-section and diameter, such that the lancet can be mounted on the lancet holder and protrude at a predetermined length in releasing and the lancet needle can vertically protrude through the through-hole of the cover and damage only a predetermined target portion of a subject.

Further, lancets with different cross-sections are available.

BEST MODE

Figure 1:
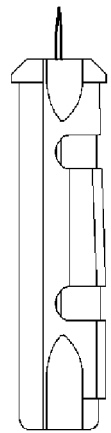
FIG. 1 is a view comparing the cross-sections and diameters of six lancets.
Figure 1:
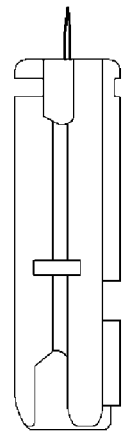
Figure 1:
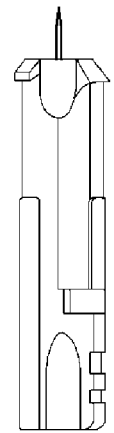
Figure 1:
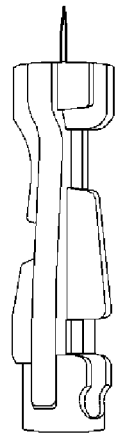
Figure 1:
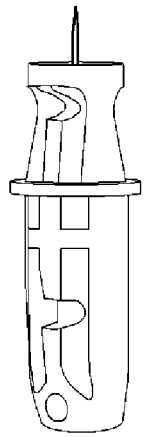
Figure 1:

Hereinafter, exemplary embodiment of the present invention will be described in detail with reference to the accompanying drawings. First, when giving the components in the drawings reference numerals, it should be noted that the same reference numerals are given to reference numerals as same as possible even if they are shown in different drawings. Further, the in description of the present invention, the detailed description of related well-known configurations and functions is not provided, when it is determined as making the scope of the present invention unclear.

Figure 2:
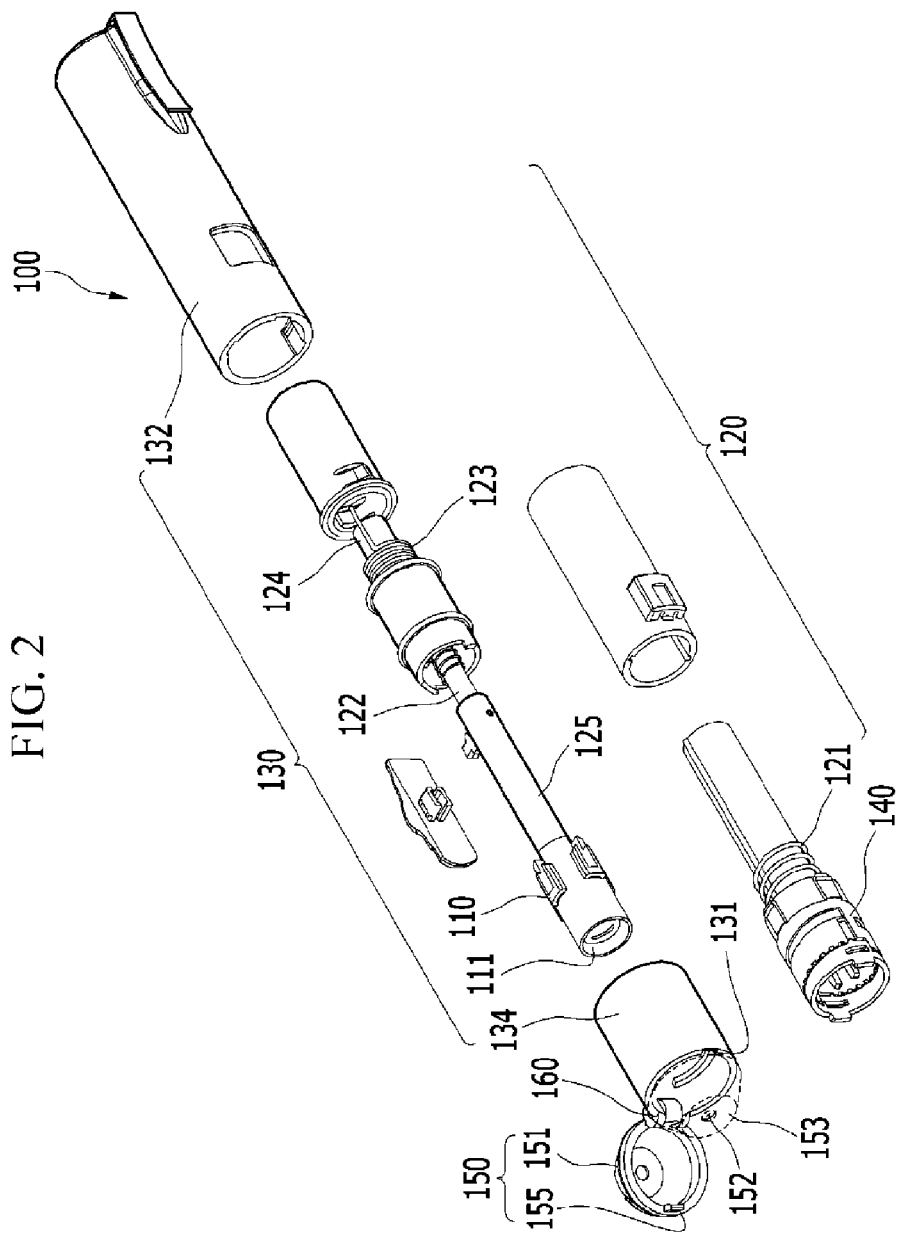
FIG. 2 is a partial exploded perspective view showing a lancet device according to an exemplary embodiment of the present invention.
Figure 3:
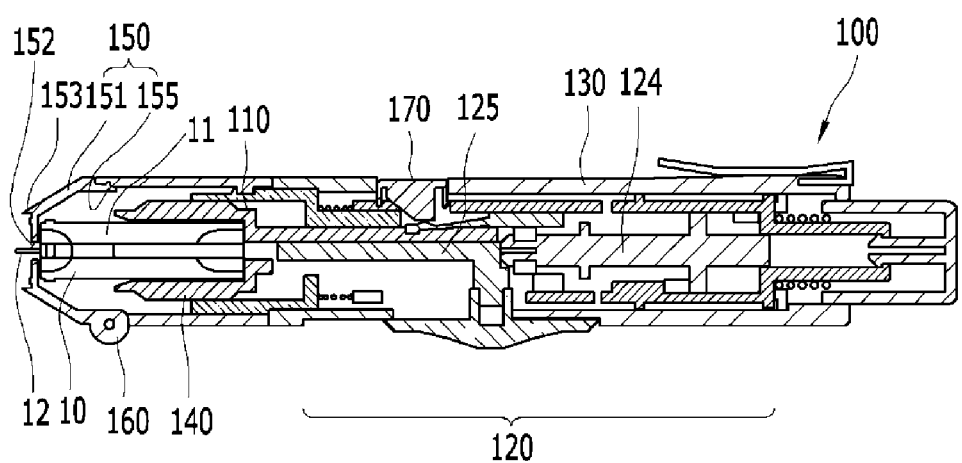
FIG. 3 is a cross-sectional view of the assembly of the parts shown in FIG. 2.
Figure 4:
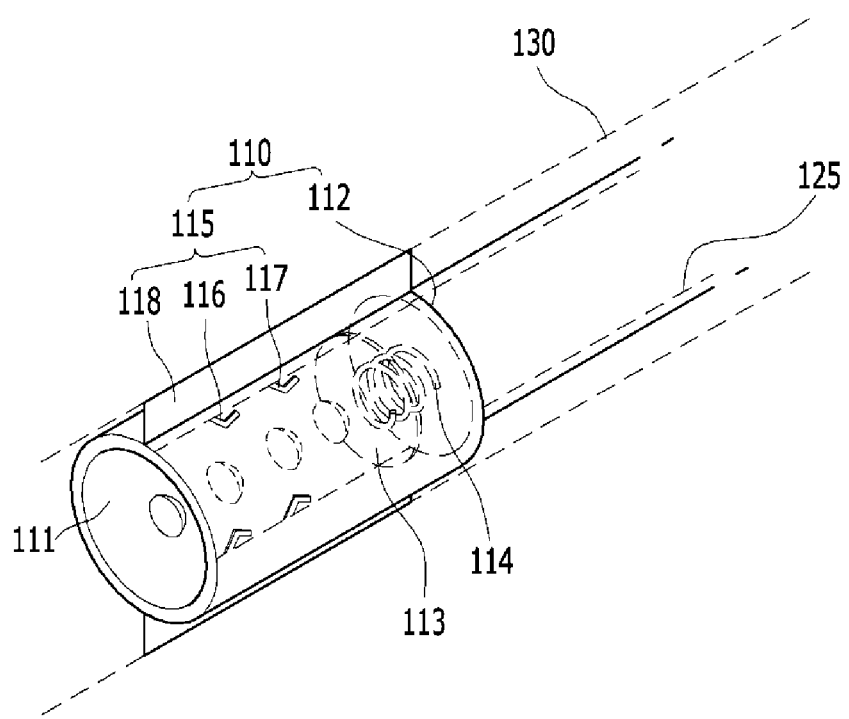
FIG. 4 is a perspective view of a lancet holder in the lancet device according to an exemplary embodiment of the present invention.
Figure 5:
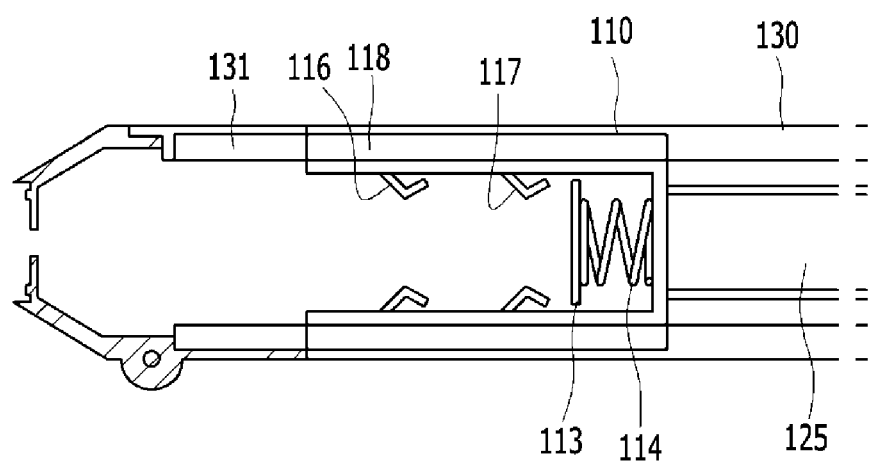
FIG. 5 is a side cross-sectional view of FIG. 4.
Figure 6:
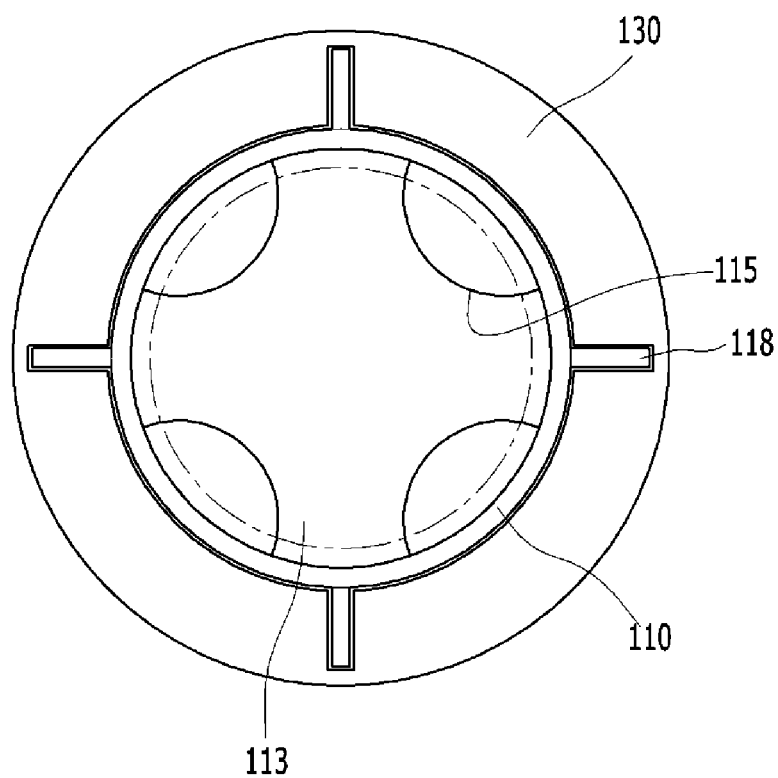
FIG. 6 is a front view of FIG. 4.

Referring to FIGS. 2 and 3, a lancet device 100 according to an exemplary embodiment of the present invention includes a lancet holder 110, an operating mechanism 120, a housing 130, an operation switch 170, a cover 150, a coupling portion 160, and a depth adjusting member 140.

The lancet holder 110 has a lancet seat 111 to mount a lancet 10 at one end and is disposed at a side in the housing 130.

The lancet 10 (see FIG. 7), which is disposable, has a lancet needle 12 at one end of a lancet body 11 with a predetermined length and the lancet needle 12 is combined with a protection cap 13.

The protection cap 13 is coupled to one end of the lancet needle 12 by insert injection, and according to this configuration, the protection cap 13 can be separated from the lancet needle 12 even by a small force.

The operating mechanism 120 is disposed at the other end of the lancet holder 110, has a structure for loading and releasing the lancet holder 110 along a predetermined path, and for this operation, it includes a plurality of springs 121, 122, and 123, as shown in FIG. 2.

The housing 130, a cylinder sized to be portable by a user, receives the operating mechanism 120, with the lancet holder 110 coupled to one end, and the operation switch 170 operating with the operation mechanism 120 is disposed at a predetermined position.

The operation switch 170 is connected to the operating mechanism 120 and operates the operating mechanism 120 by pressing it.

The cover 150 covers one end of the housing 130 and has a through-hole 152 at the center through which the lancet needle 12 of the lancet 10 instantaneously protrudes.

The coupling portion 160 hinges one end of the housing 130 with the cover 150, such that the cover 150 pivots to open/close at 180 degrees.

The depth adjusting member 140 adjusts the penetration depth under the skin of the lancet needle 12.

To this end, as shown in FIG. 2, the housing 130 includes a first housing part 132 receiving the operation mechanism 120 and a second housing part 134 rotating about the axis of the first housing part 132 and combined with the depth adjusting member 140 therein.

The second housing part 132 is combined with the cover 150 and the depth adjusting member 140 and the distance between the through-hole 152 and the lancet needle 12 is adjusted by rotating the cover 150 or the second housing part 132.

When a user presses the operation switch 170, the springs 121, 122, and 123 are instantaneously compressed, and extend and hit a movable shaft 125 under which a shock transmission rod 124 is positioned, the movable shaft 125 hits the lancet holder 110 holding the lancet 10, and the lancet 10 protrudes outward.

It is preferable that the lancet 10 instantaneously protrudes vertically through the through-hole 152 of the cover 150 when being released in order to reduce the pain of a subject, and for this operation, the lancet 10 has to be firmly mounted on the lancet holder 110 and kept in the position.

A preferable structure of the lancet holder 110 is described below with reference to FIGS. 4 to 7.

The lancet holder 110 includes a holder body 112, an elastic fixing portion 115, a lancet plate 113, an elastic support member 114, and a guide wing 118.

The holder body 112 has the lancet seat 111 at one end to mount the lancet 10 and receives the lancet 10.

The elastic fixing portion 115 is formed in a pair, facing each other, on the inner side of the holder body 112 to keep the lancet 10 vertical in the holder body 112 and elastically fixes the lancet 10.

That is, in an exemplary embodiment of the present invention, a plurality of elastic fixing portions 115 is arranged radially at predetermined angles around the inner side of the holder body 112 and is plate-shaped members protruding inward.

The elastic fixing portion 115 include a first fixing member 116 and a second fixing member 117.

A plurality of first fixing members 116 is arranged radially at predetermined angles around the inner side of the upper end of the holder body 112 and fixes one end of the lancet 10.

A plurality of second fixing members 117 is arranged radially at predetermined angles around the inner side of the lower end of the holder body 112 and fixes the other end of the lancet 10.

In other words, the first fixing members 116 and the second fixing members 117 fix the upper end and the lower end of the lancet body 11 so that the lancet body 11 is firmly fixed to the lancet holder 110.

To this end, it is preferable that the first fixing members 116 and the second fixing members 117 are four pieces, respectively, that is, the elastic fixing portion 115 is composed of eight pieces.

According to the structure of the elastic fixing portion 115, even if the lancets 10 are different in cross-section and diameter, the lancet holder 110 can accurately keep all of lancets vertical, and therefore, the lancet 10 can be mounted on the lancet holder 110 and protrude at a predetermined length in releasing and the lancet needle 12 can vertically protrude through the through-hole 152 of the cover 150 and damage only a predetermined target portion of a subject.

That is, since the lancet 10 is positioned at the center of the lancet holder 110 and moves straight forward at the center without curving, it can accurately prick one point without pricking a skin at an angle, thereby reducing the pain.

Further, it is preferable to fix the movable shaft 125 to the underside of the holder body 112 so that the lancet can vertically move forward without the movable shaft 125 and the holder body 112 shaking even under hitting from the shock transmission rod 124. The moveable shaft 125 may be coupled to an underside of the holder body 112 for releasing and moving the lancet needle 12.

The lancet plate 113 is arranged such that the lower end of the lancet 10 faces the bottom of the holder body 112.

The elastic member 114, which is a spring, is disposed under the lancet plate 113 and compensates for the variable length of the lancet 10.

Since the lengths of lancets can be compensated by the lancet plate 113 and the elastic support member 114 even if the lengths are different, the lancet holder 110 can receive lancets having various lengths.

The guide wing 118, which is a plate, is longitudinally elongated along the outer side of the holder body 112 and moves along a releasing guide groove 131 formed on the inner side of the housing 130 receiving the holder body 112.

Therefore, it is possible to minimize the possibility of the lancet 10 coming out from the vertical direction and to stably move the lancet 10 forward, in releasing.

Figure 7:
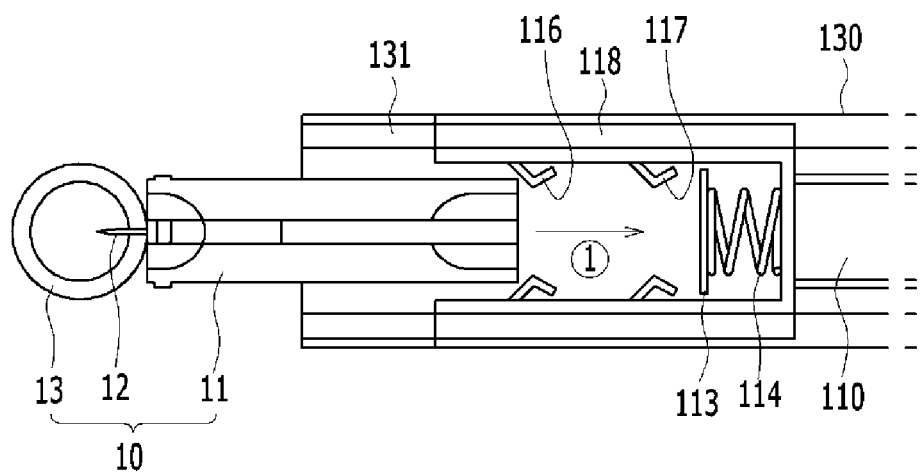
FIG. 7 is an operation view illustrating a change in internal structure of the lancet holder, when a lancet is mounted on the lancet holder and then released.
Figure 7:
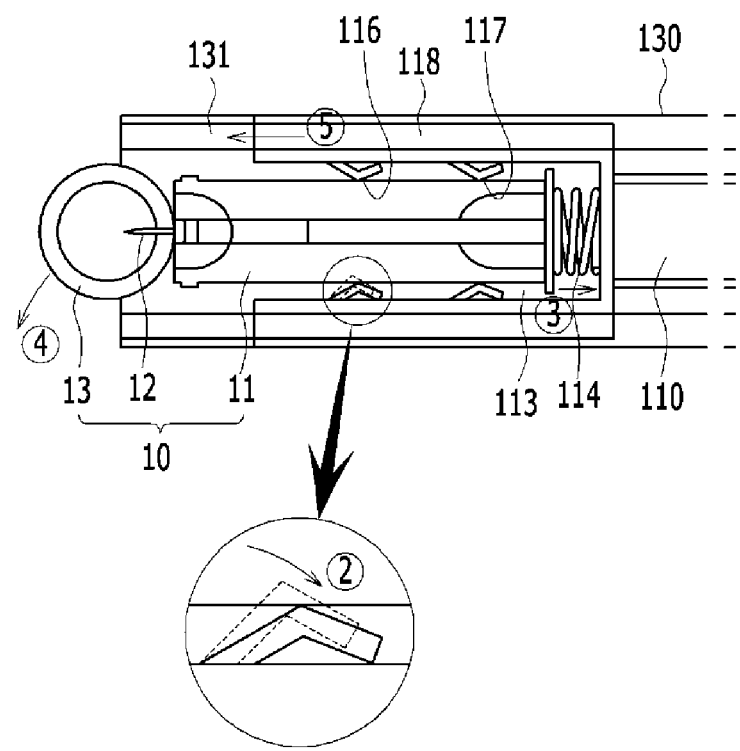

The above description is explained below with reference to FIG. 7.

First, the lancet 10 is pushed into lancet holder 110 (①) with the cover 150 separated from the housing 130, in which the elastic fixing portion 115 is bent to the inner side of the lancet holder 110 by the elastic force of the elastic fixing portion 115 to fit to the diameter of the lancet 10.

The bending fixing portion 115 is in close contact with the outer side of the lancet body 11 by a restoring force, such that the lancet 10 can be firmly fixed to the lancet holder 110.

The lancet plate 113 and the elastic support member 114 move to the underside of the lancet holder 110 in accordance with the length of the lancet 10.

Next, when the protection cap 13 is separated from the lancet 10 fixed to the lancet holder 110 (④) and then the cover 150 is mounted on one end of the housing 130 and the operation switch 170 is pressed, the guide wing 118 of the lancet holder 110 vertically moves forward along the releasing guide groove 131 of the housing 130 (⑤).

The above description is an example of the spirit of the present invention and may be changed and modified in various ways by those skilled in the art without departing from the scope of the present invention. Therefore, the exemplary embodiments described herein are not for limiting the spirit of the present invention, but for explaining the present invention and the scope of the present invention is not limited to the exemplary embodiments. The protective range of the present invention should be construed by claims and the equivalents should be construed as being included in the scope of the present invention.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A lancet device comprising:
   a housing;
   a lancet holder mounted to the housing, and comprising:
      a holder body having a cavity defining a lancet seat at a first end of the holder body for receiving a lancet needle;
      a plurality of elastic fixing portions arranged in pairs to face each other on an inner side of the cavity of the holder body operable to engage the lancet needle so that the lancet needle received in the cavity of the holder body is vertically held, and elastically fixing the lancet needle;
      a lancet plate operable to engage the lancet needle, the lancet plate disposed within the cavity of the holder body;
      an elastic support member disposed within the cavity of the holder body, under the lancet plate, and configured to compensate for a variable length of the lancet needle; and
   a movable shaft coupled to an outer surface of the holder body for releasing and moving the lancet needle.

2. The lancet device of claim 1, wherein the plurality of elastic fixing portions are arranged at predetermined angles around the inner side of the cavity of the holder body.

3. The lancet device of claim 2, wherein the plurality of elastic fixing portions include:
   a plurality of first fixing members arranged at predetermined angles around the inner side of the cavity of the holder body and adjacent to an open end of the cavity of the holder body; and
   a plurality of second fixing members arranged at predetermined angles around the inner side of the cavity of the holder body, wherein the plurality of second fixing members are positioned proximally to the plurality of first fixing members.

4. The lancet device of claim 3, wherein the plurality of elastic fixing portions are plates protruding inward.

5. The lancet device claim 1, further comprising a guide wing elongated longitudinally along the outer surface of the holder body and operable to move along a releasing guide groove formed on an inner side of the housing.

6. The lancet device of claim 2, wherein the plurality of elastic fixing portions are plates protruding inward.

* * * * *